United States Patent
Hopenfeld

[19]

[11] Patent Number: 5,982,959
[45] Date of Patent: Nov. 9, 1999

[54] COATED FIBER OPTIC SENSOR FOR THE DETECTION OF SUBSTANCES

[76] Inventor: Joram Hopenfeld, 1724 Yale Pl., Rockville, Md. 20850

[21] Appl. No.: 09/114,030

[22] Filed: Jul. 11, 1998

Related U.S. Application Data

[62] Division of application No. 08/707,870, Sep. 9, 1996, Pat. No. 5,828,798.

[51] Int. Cl.$^6$ ....................................................... G02B 6/00
[52] U.S. Cl. .............................. 385/12; 385/13; 385/128; 250/227.14; 250/301
[58] Field of Search ................................. 385/12, 13, 123, 385/128; 250/227.11–227.25, 301, 302, 303

[56] References Cited

U.S. PATENT DOCUMENTS

| | | |
|---|---|---|
| 4,159,420 | 6/1979 | Tsunoda . |
| 4,270,049 | 5/1981 | Tanaka et al. . |
| 4,386,269 | 5/1983 | Murphy . |
| 4,764,671 | 8/1988 | Park . |
| 4,846,548 | 7/1989 | Klainer ........................................ 385/12 |
| 5,005,005 | 4/1991 | Brossia et al. . |
| 5,015,843 | 5/1991 | Seitz et al. . |
| 5,052,820 | 10/1991 | McGinniss et al. ................ 250/227.11 |
| 5,187,366 | 2/1993 | Hopenfeld . |
| 5,200,615 | 4/1993 | Hopenfeld . |
| 5,262,638 | 11/1993 | Egalon et al. ....................... 250/227.14 |
| 5,340,715 | 8/1994 | Slovacek et al. . |
| 5,343,037 | 8/1994 | Berkcan .............................. 250/227.21 |
| 5,378,889 | 1/1995 | Lawrence . |
| 5,525,800 | 6/1996 | Sanghera et al. . |
| 5,532,493 | 7/1996 | Hale et al. . |
| 5,712,934 | 1/1998 | Johnson . |
| 5,804,453 | 9/1998 | Chen ......................................... 385/12 |

OTHER PUBLICATIONS

Gialiorezi et. al. "Optical Fiber Sensors Challenge the Competition" IEEE. Spectrum Sep. 1986.

J.D. Bronzino Biomedical Engineering HBK; CRC. IEEE, 1995 pp. 768 & 776.

C.J. McNeil, et al. "Electrochemical Sensors Based on Impedence Measurement of Enzyme–Catlyzed polymer dissolution". Thery & Applications Anal. Chemistry 67, No. 21 1995 pp. 3928–3935.

P. N. Barlett et. al "Enzyme Switch Responsive to Glucose" Anal. Chem. 1993, 65 1118–1119.

J. S. Scultz "Biosensors" Scientific American, Aug. 1991, 64–71.

O.S. Wolfbeis "Fiber Optic Biosensors Based on Molecular Recognition" Sensors & Actuators, 1991, 5 pgs.

TH. Scheper et al. "Optical Sensors for biotechnological applications" Biosensors & Bioelectronics 9 (1994) 83.

*Primary Examiner*—Hemang Sanghavi
*Attorney, Agent, or Firm*—Bruce Hopenfeld

[57] ABSTRACT

The present invention provides methods and apparatus for inexpensively and accurately sensing with the use of a fiber optic guide the presence or absence of a particular substance ("analyte"). The preferred embodiment of the sensor of the present invention comprises a light source, a photodetector, and a loop shaped plastic fiber that is exposed to the environment and that acts as a sensing element. In the preferred embodiment, the fiber optic guide comprises a core and a cladding, either of which are coated with a coating that is selected to at least partially degrade in the presence of the analyte. The coating is selected to have an index of refraction below that of the core but sufficiently large to allow at least some light to escape from the core even in the absence of the analyte. A decrease in the amount of light is detected when the analyte is present. Alternatively, the coating is selected to have an index of refraction just above or greater than the core, causing an increase in the amount of light that is detected when the analyte is present.

19 Claims, 11 Drawing Sheets

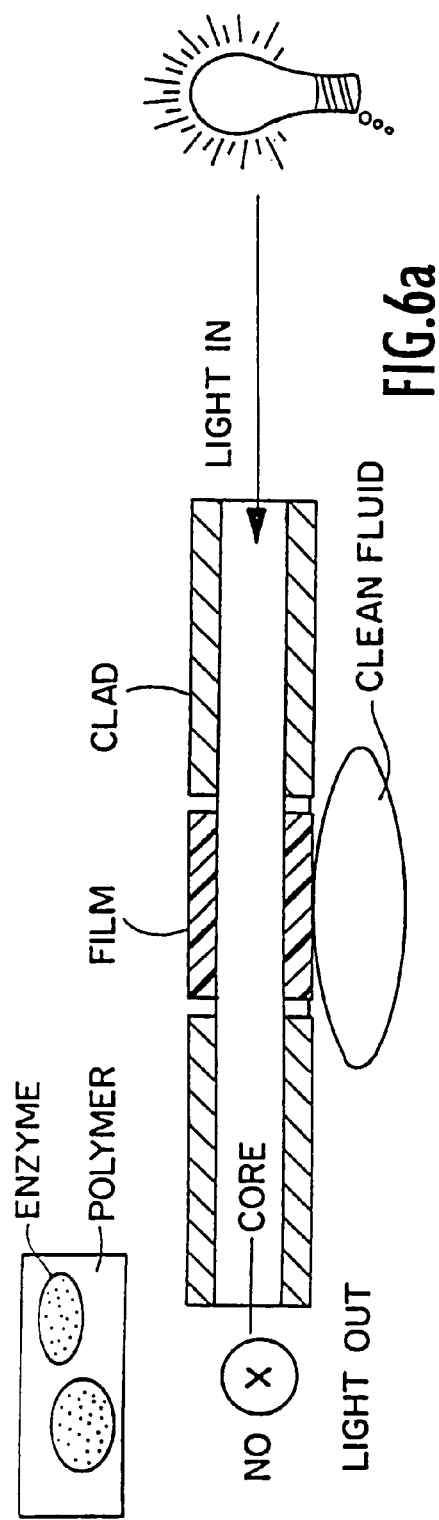
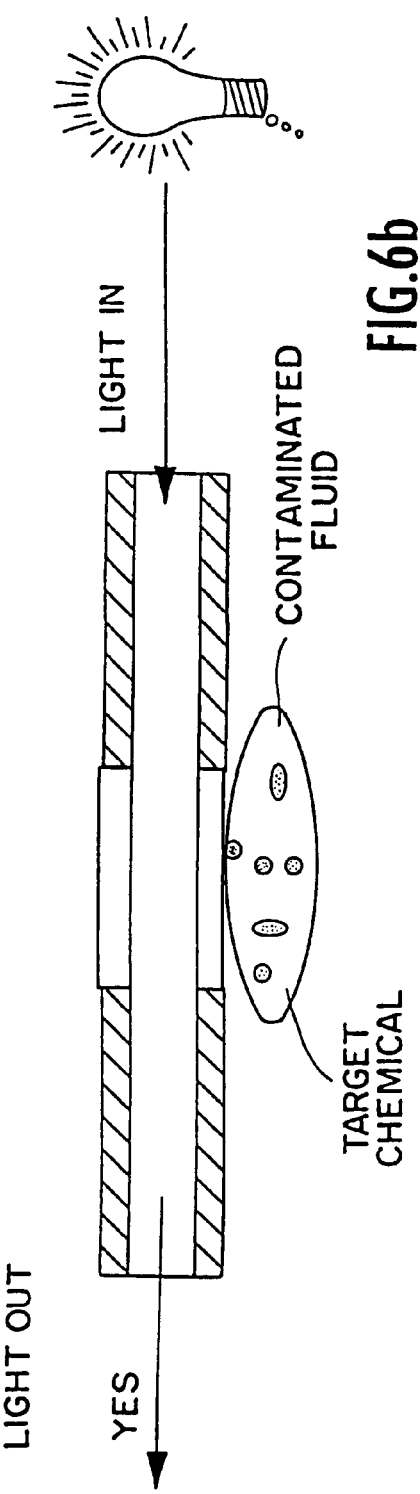
FIG.6a
FIG.6b
FIG.6c

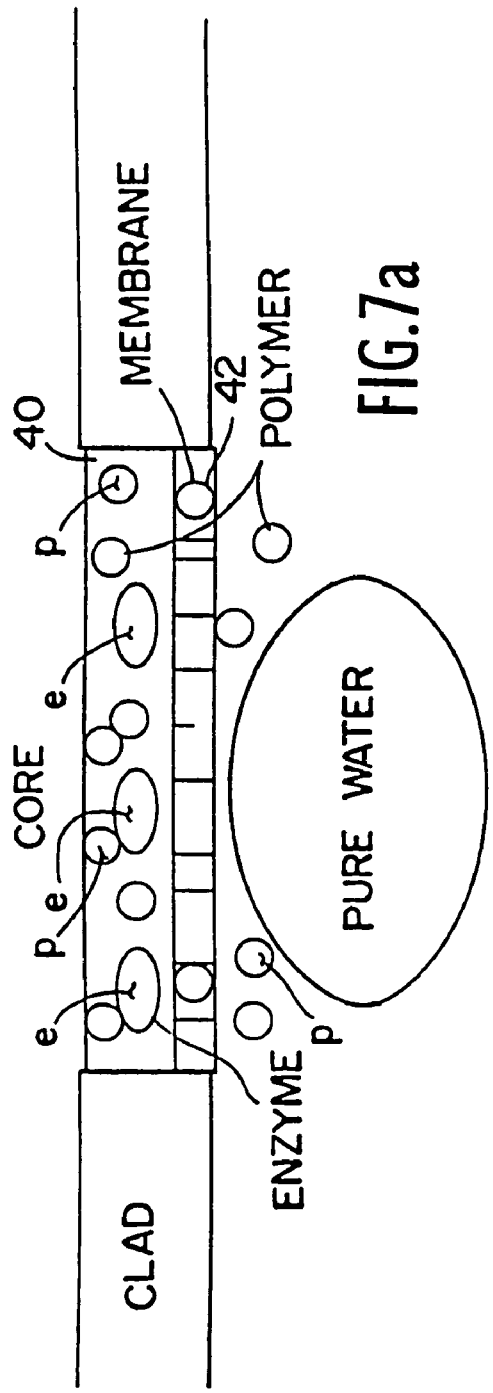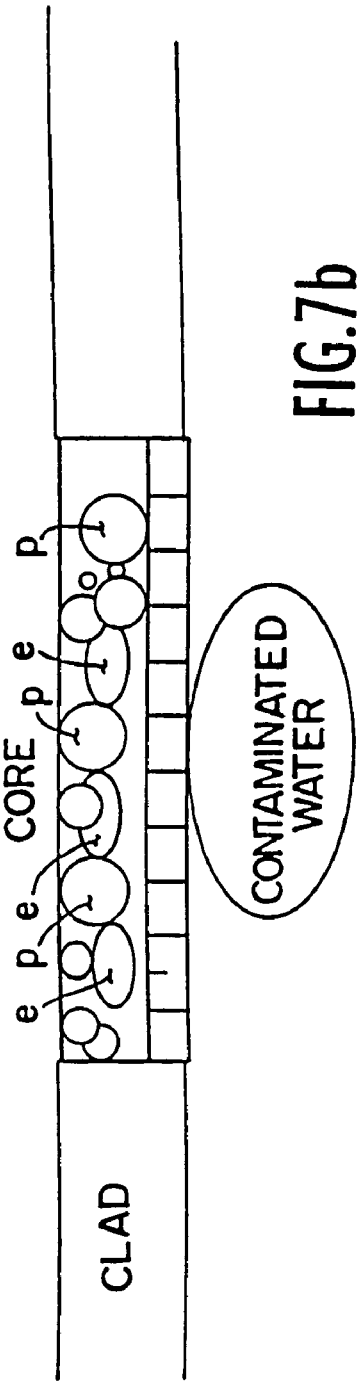

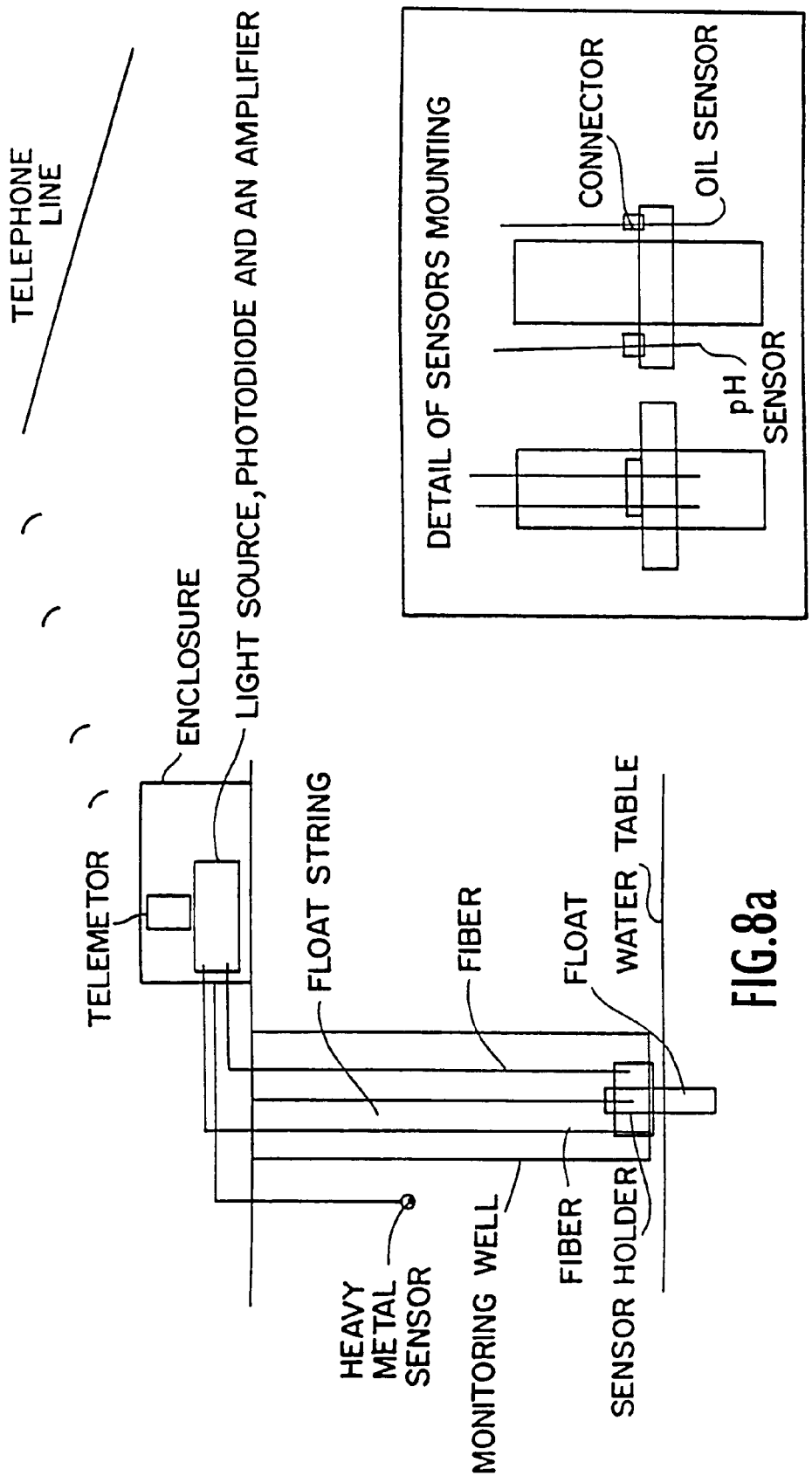

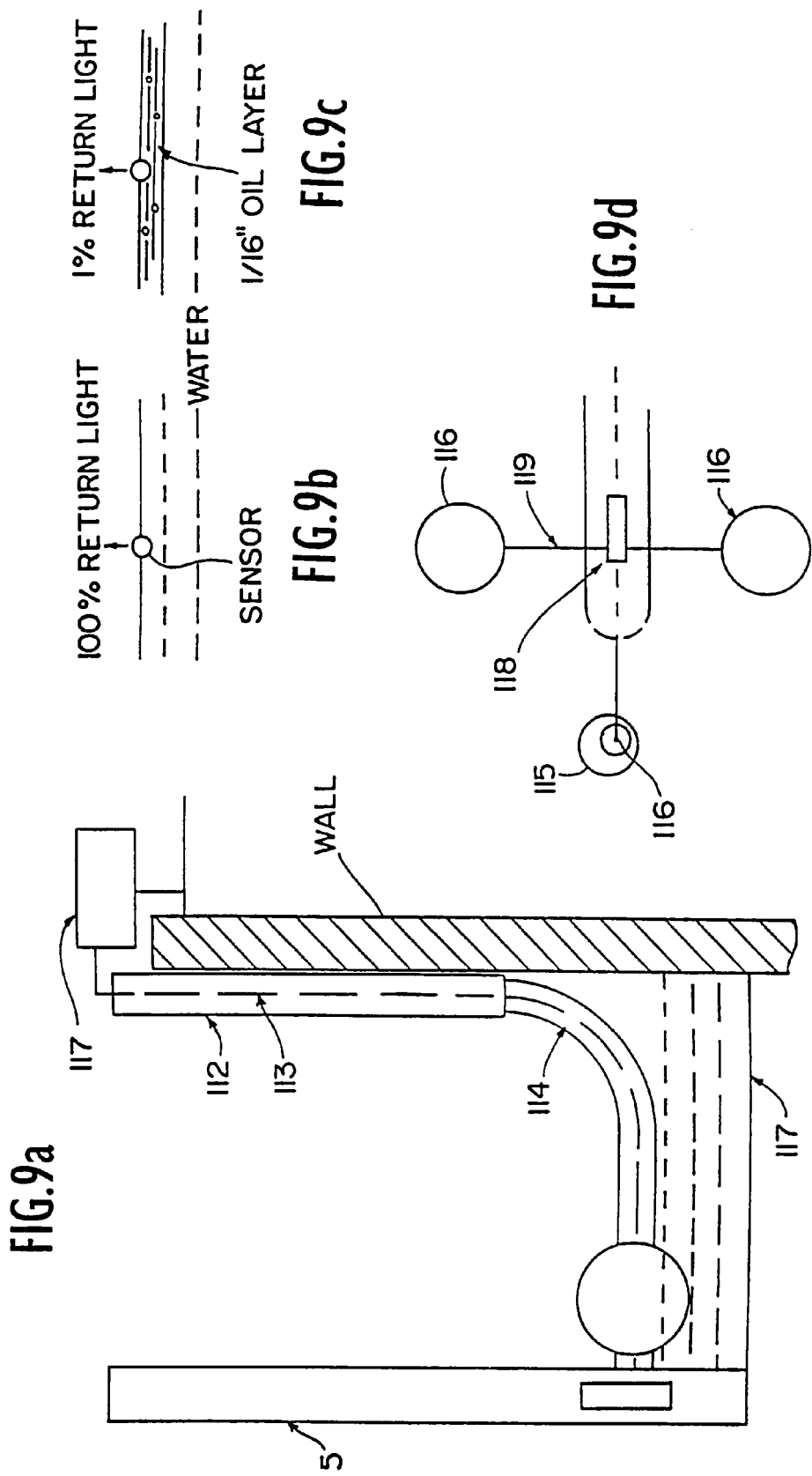

201-FIBER
202-POLYMER
203-WIRE

COATED FIBER OPTIC SENSOR FOR THE DETECTION OF SUBSTANCES

RELATED APPLICATION

This application is a divisional of Ser. No. 08/707,870 filed Sep. 9, 1996 now, U.S. Pat. No. 5,828,798, entitled "Looped Fiber Optic Sensor for the Detection of Substances," filed Sep. 9, 1996.

BACKGROUND OF THE INVENTION

1. Field of the Invention

The invention relates to sensors, and more particularly, to fiber optic sensors for detecting the presence or absence of a particular substance.

2. Art Background

Sensors that can detect the presence or absence of a selected substance ("analyte") are widely used in many different fields. For example, environmental sensors are used to detect pollutants and have become increasingly important as environmental standards have become stricter. Medicine is another field where the use of sensors is growing, especially in the area of medical diagnostics. As yet another example, sensors also control various industrial processes. Indeed, sensors perform important functions in many other fields and will undoubtedly find many new applications in the future.

There are many different types of prior art sensors. Fiber optic sensors have increased in popularity due to the ability of a fiber optic cable to inexpensively and accurately carry a signal over long distances.

Prior art fiber optic sensors, however, are not optimal. Prior art fiber optic sensors are either very expensive, inaccurate, or limited in the distance over which they may be used. For example, according to one of the more effective prior art fiber optic sensors, a U shaped fiber is employed for the detection of liquid levels in tanks. See FIG. 1. The U bend is exposed to a liquid, and a light source provides light which is guided to the U bend, where some of it escapes to the environment. Light that does not escape passes through the U bend and is detected by a detector. Because different liquids have different indices of refraction, the amount of leakage through the U bend, and therefore the strength of the signal through the fiber, depends upon the type and/or amount of liquid in contact with the U bend. Thus, continuous monitoring of the variation of the light intensity is used to measure the liquid level in the tank and may also be used to detect the presence of a different liquid in the tank.

However, in practice, prior art U bend sensors do not provide a very strong signal and generally require a relatively high powered, and therefore expensive, light source, especially where the detector must be located far from the U bend portion.

Another scheme to improve the effectiveness of the sensor involves coating the sensor with a substance that dissolves in the presence of a liquid to be detected. When the liquid to be detected is present, it dissolves, thus bringing the sensor directly into contact with its environment and increasing the light loss from the sensor, thus creating a signal. Other schemes include coating a fiber's core with porous soluble materials which change their optical properties based upon the presence/absence of a liquid to be detected.

Again, however, in practice, these mechanisms do not prove particularly effective. In particular, when used in conjunction with present sensor geometries (eg. the U bend described above or a straight line), these schemes generate weak signals per unit area of the fiber and therefore a substantial segment of the fiber must be used as a sensing element and very sensitive, and therefore expensive, detectors are required. Furthermore, because of the fragility of the fibers, it is difficult to package such long sensors or use them in small fluid samples where access to the sample is restricted. Still further, the prior art dissolution mechanisms rely on the presence of a liquid and do not provide for the detection of a solute in a solvent.

The present invention improves the state of the art by, among other things, optimizing the geometrical configuration of the sensor, thus providing a very compact, sensitive mechanism for producing a strong signal. Consequently, the sensors' response to different fluids and chemicals can be accurately monitored from remote locations with off-the-shelf compact light source/detector pairs.

SUMMARY OF THE INVENTION

The present invention provides methods and apparatus for inexpensively and accurately sensing, with a fiber optic guide, the presence or absence of a particular substance ("analyte"). The preferred embodiment of the sensor of the present invention comprises a light source, a photodetector, and a loop shaped plastic fiber that is exposed to an environment and that acts as a sensing element. A light originating at the light source is guided through the loop shaped fiber. Some light continues through the loop shaped fiber and is detected by the photodetector whereas other light may escape to the environment through the loop shaped fiber. The amount of light that escapes to the environment, and therefore the amount of light received by the photodetector, depends upon whether the analyte is present.

The loop shape of the plastic fiber causes different amounts of light to be received by the photodetector depending upon whether or not the analyte is present in the environment. In the preferred embodiment, the loop comprises approximately one half of an ellipse with a relatively small minimum radius of curvature. The angles at which the light enters and exits the loop's sensing zone are defined by the tangents to the elliptical arc. The geometry of the loop may be adjusted depending upon the characteristics of the sensor's normal environment and the analyte. Thus, the present invention allows for an optimal sensor shape to be chosen based upon the substance or substances comprising the normal environment and the analyte.

Further, according to the present invention, the fiber optic guide is coated with a coating that is selected to decompose in the presence of the analyte. According to one embodiment, unlike prior art sensors, the coating is selected to have an index of refraction just above or greater than the fiber optic guide. Thus, the coating's removal causes an increase, not a decrease, in the detected signal strength. In an alternate embodiment, the coating swells, rather than dissolves, in the presence of the substance to be detected.

In the preferred embodiment, the coating comprises a combination of polymers and enzymes. A polymer is selected to dissolve or swell when the local pH changes (i.e. when the detectable substance is present) and an enzyme is selected that causes these changes in a selective manner.

In yet another alternate embodiment, the fiber optic guide is coated with a polymer that bends the tube into a desired shape upon contact with the analyte.

The combination of the shape and interface mechanisms of the present invention provides for an inexpensive, accurate sensor with an almost limitless variety of applications. For example, and in no way limiting the applications of the present invention, the sensor of the present invention may be used to detect: the presence of one liquid in another liquid, the pH level of a liquid, the level of urea in blood, the presence of heavy metals in a liquid and the presence of antigens in drinking water. Many other applications and other advantages of the invention will be apparent from the following description.

BRIEF DESCRIPTION OF THE DRAWINGS

FIGS. 6a and 6b diagrammatically illustrate coating the core or cladding of a fiber optic guide in the sensing zone with a coating, with an index of refraction greater than the fiber optic guide, that is selected to decompose in the presence of the analyte. FIG. 6c is an expanded view of an embodiment of a coating shown in FIG. 6a.

FIGS. 7a and 7b illustrate an alternate interface between the fiber optic guide and its environment that is useful for "one shot" as opposed to continuous detection schemes.

FIGS. 8a and 8b illustrate a system to use sensors for soil and ground monitoring.

FIGS. 9a, 9b, 9c and 9d illustrate a system to use sensors for detecting oil spills in water.

DETAILED DESCRIPTION OF THE INVENTION

The present invention discloses methods and apparatus relating to fiber optic sensors. Although the present invention is described with reference to specific circuits, block diagrams and signals, etc., it will be appreciated by one of ordinary skill in the art that such details are disclosed simply to provide a more thorough understanding of the present invention. It will therefore be apparent to one skilled in the art that the present invention may be practiced without these specific details. In other instances, well known circuits are shown in block diagram form in order not to obscure the invention unnecessarily.

Section I describes the sensor of the present invention. Section II briefly describes various applications of the sensor described in Section I. Section III includes examples of systems, utilizing the sensor of the present invention, for detecting various analytes in various environments.

I. System Overview and Theoretical Considerations

Figure 1:
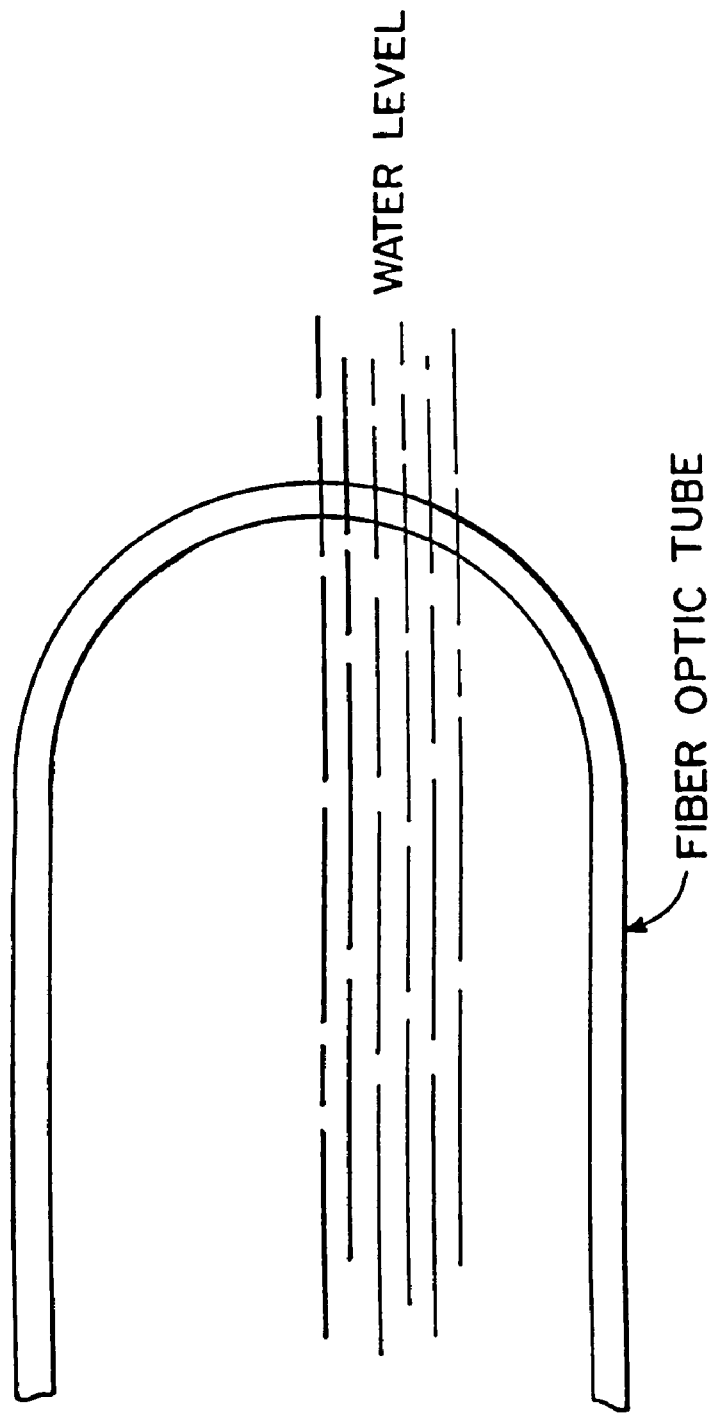
FIG. 1 illustrates a prior art fiber optic sensor.
Figure 2:
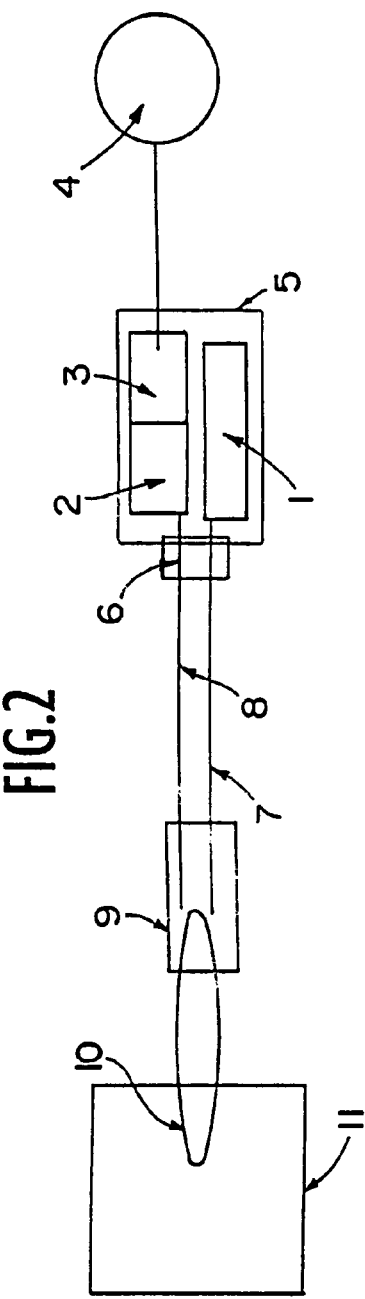
FIG. 2 illustrates a preferred embodiment of the sensor of the present invention.

FIG. 2 illustrates a preferred embodiment of the sensor of the present invention. The preferred embodiment comprises a light source 1, a photodetector 2, an amplifier 3, an electrical switch 4, an enclosure 5, an enclosure connector 6, two fiber optic guides 7 and 8, a sensor connector 9, and a loop shaped plastic fiber 10 which incorporates a sensing element which is exposed to an environment 11, which may comprise any type of environment (liquid, solid, gas or combinations thereof). A light originating at the light source, which may comprise an LED, a laser or any other type of light source, enters the fiber 7 which is connected to one side of the sensor 10 through the connector 9. The light passes through the sensor and through the connector 9 then enters the second fiber 8. The other end of the fiber 8 enters the enclosure 5 through connector 6 where it is attached to the photodiode 2 which in turn is juxtaposed to the amplifier 3.

When it is desired to monitor the presence or absence of an analyte in the environment 11, the sensor is disposed within the environment 11 and its response is monitored by status of the switch 4. The switch 4 may be connected to a relay, an LED, or a sound generating device. In the absence of the target chemical, most of the light which is emitted from the source 1 arrives to the photodetector 2. In this state, the switch 4 is in the off position. When the analyte is present in the environment 11, the sensor 10 either acts like a gate which allows the light to escape into the environment 11 or decreases the amount of light escaping into the environment 11. In either case, the different light signal arriving to the photodiode 2 changes the state of the amplifier 3 which closes the switch 4.

It should be noted that the present sensors may be used in hostile environments. When used in hostile environments, plastic fiber instead glass fiber is the material of choice for the sensor of the preferred embodiment. In the preferred embodiment, the optical fiber is a commercially available fiber optic guide such as Toray sold by MORITEX USA, These fibers are the preferred choice because of ruggedness and ease of sensor fabrication. While plastic fiber is robust, inexpensive, and easy to connect, its light transmission characteristics are poor in comparison to glass. Thus, instabilities such as dirt buildup, moisture, temperature fluctuations and tube bends, which may inadvertently be introduced during installation, should be avoided. Otherwise, the combination of these factors may produce false signals (negative or positive).

To minimize such nuisance signals, the energy arriving to the detector 2 must be larger than the instabilities to prevent the amplifier 3 from changing state (on or off). This feature, commonly known as excess gain, can be calculated by dividing the energy at the photo detector 2 by the threshold energy of the amplifier 3. An excess gain ratio of 50 allows operation in very demanding environments. The recognition signal sent by the sensor to the detector 2 must exceed the excess gain to activate the switch.

The present invention employs a sensor 10 with a novel shape that greatly increases the sensor's sensitivity and thus allows for operation in environments with large attendant excess gains. In addition, the present invention provides a novel interface between the sensor and its environment. Before these features are described, the theory regarding light propagation in fiber optic guides will be briefly discussed.

Figure 3:
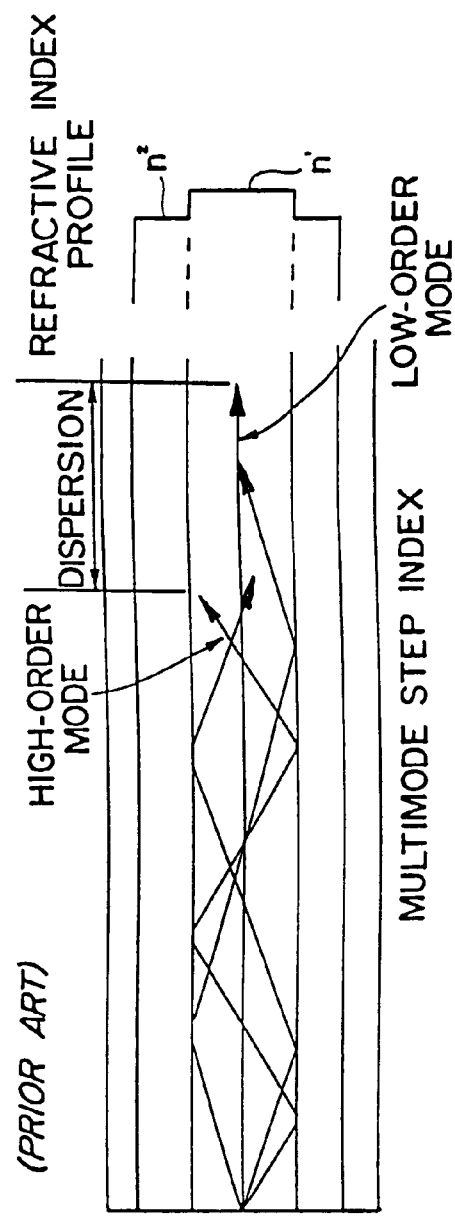
FIG. 3 illustrates light rays entering a multimode fiber optic line.

In a multimode optical fiber, which comprises a core and a cladding, light rays enter the fiber at different angles and strikes the core/clad interface at angles which exceed the critical angle, as illustrated in FIG. 3. Because the light enters the fiber at different angles it travels along its length at different modes. The lowest mode is represented by the straight ray which travels along the axis of a straight fiber. With the exception of a small fraction of light which travels through the cladding, most of the light is bound within the core of the fiber.

According to the present invention, leakage from the core can be created by bending the fiber and thereby changing the refraction pattern at the core/clad interface. Unlike the straight fiber, in the curved portion of the fiber some light modes may strike the core/clad interface at angles which differ from the critical angle. If the bent area is used as a sensor, the bend configuration must be optimized for the intended application. Excessive bending will strain the outer planes of the fiber and reduce the energy at the photodetector. Insufficient bending on the other hand will not produce sufficient sensitivity to changes in the refractive index of the sensor's environment.

Losses in a bend consist of a pure bending loss and a transition loss. The transition loss occurs in the region where the straight fiber enters the curved fiber. The increase in abruptness of this point increases the number of the lower mode rays which are refracted into the fluid. The degree of refraction strongly depends on the geometry, as will become apparent in this disclosure.

Thus, a sensor's shape is crucial to its operation. In addition, the interface between the environment and the fiber optic guide is also critical because the amount of light that escapes from the fiber depends in part on the indices of refraction of the sensor and its environment. The present invention presents novel features with respect to the sensor shape and the interface between the environment and the fiber optic guide. These two features of the present invention will be discussed in turn.

1. Sensor Shape

Figure 4:
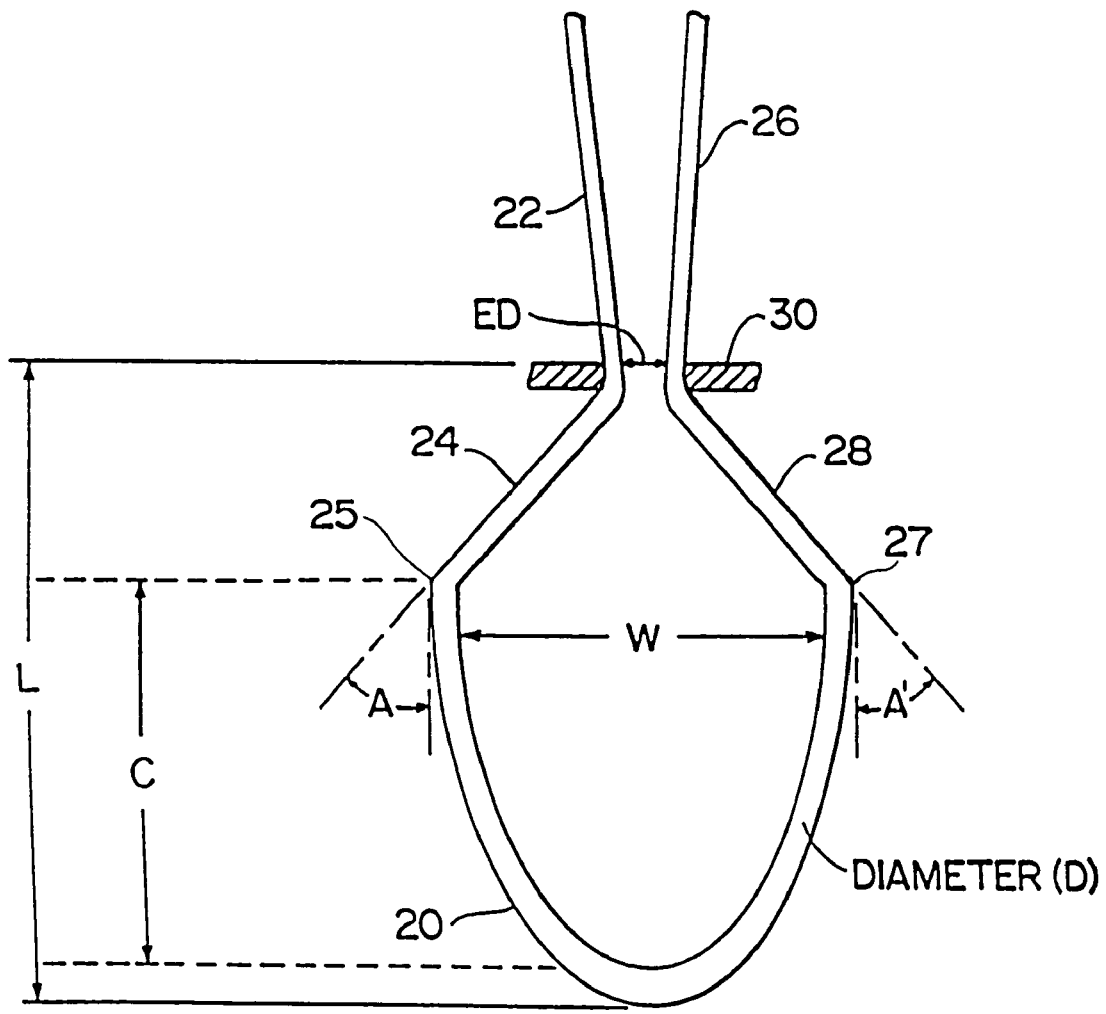
FIG. 4 illustrates the preferred sensor shape of the present invention.

FIG. 4 illustrates the preferred sensor 10 shape of the present invention. As shown, the sensor 10 comprises a sensing segment 20 and guiding sections 22, 24, 26 and 28 joined with a tie 30. The sensing segment 20 is shaped in form of a partial ellipse that comprises approximately one half of an ellipse and the two segments 24 and 28 form a substantially "v" shape with respect to one another, and the two segments 22 and 26 also form a substantially "v" shape with respect to one another. The sensing segment 20 along with the guiding segments 24 and 28 form a shape defined by a length (L), width (W), angle (A) and a sensing element length (C), as shown. (C, L and W are measured to the inside of the fiber optic guide as shown). When the fiber optic guide comprises plastic, the exact final shape may be determined by the natural bending properties of the plastic as will be further described below.

The sensing segment 20 is joined to the segment 24 and 28 such that the tangent of the segment 24 and 28 at the points 25 and 27 where they meet the segment 20 are set off at an angle A from the tangents of the segment 20 at these respective points 25 and 27. In other words, the curvature of the sensor 10 is discontinuous at the points 25 and 27. In the preferred embodiment, A is given by arc tan W/2(L−C−D) and varies between 0 and 60 degrees.

Figure 5:
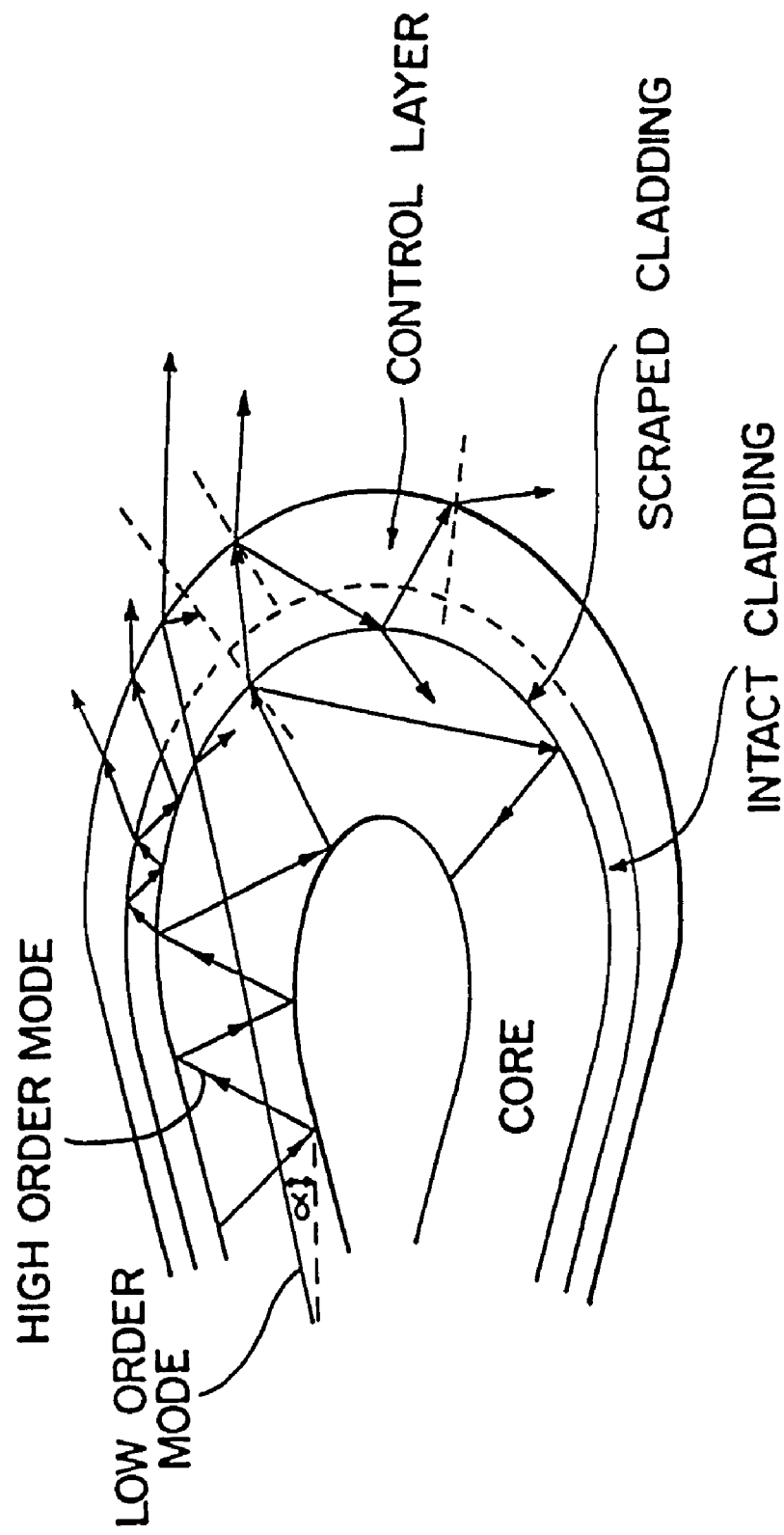
FIG. 5 is a close up view of a sensing portion of the sensor illustrated in FIG. 4.

As illustrated in FIG. 5, the fiber optic guide comprising the sensor 10 further comprises a cladding and a coating that coats the cladding, as will be further described below. In the preferred embodiment, the cladding is scraped lightly with a razor, as shown.

The values of the width W, the loop length, L, the angle A, and a diameter (D) of the fiber (including its core and cladding) significantly affect the performance of the sensor 10. Table 1 below demonstrates how different values for L and W affect light transfer between a plastic sensor and four different fluids. When the ratio (W/D) of the width W to fiber diameter D is larger than 30, the transfer or leakage of light to the environment is relatively small. Transfer or leakage, however, increases significantly as the width W decreases in loop dimension.

Snells' law can be used to explain these results. The decrease in bend width increases the number of light rays which strike the interface at angles smaller than the critical angle causing the light to "leak" from the core. As the angle A increases, an increasing number of lower modes of light strike the interface at angles which are lower than the critical angle causing further leakage, as illustrated in FIG. 5. Since light transfer in the illustrated "bulb" geometry is too complex for mathematical description, one must generally rely on experimental observations.

In particular, it has been found that for maximum sensitivity, W/D should be approximately 2 or less while L is a unique function of W and A. Table 1 can be used as a guide for the relation between the length L and the width W to attain a desired sensitivity. This relation is unique to each fiber because it depends on its strength properties. Thus, an optimal shape for a particular application may require experimenting with various shapes until a desired difference signal (between when the analyte is present and absent) is obtained.

TABLE 1

Effect of Sensor Geometry and Fluid on leakage ($\lambda$ = 650 nm, 1 mm plastic fiber, .2–.4 mm clad removed from apex)

| Dimension (mm) | | | Light Transfer to Fluid (dB) | | |
|---|---|---|---|---|---|
| L (mm) | W (mm) | C | Air (dB) | Water | Oil (dB) |
| 91 | 38 | 25 | 0.6 | 0.6 | 0.6 |
| 43 | 26 | 20 | 1.2 | 1.3 | 1.3 |
| 30 | 15 | 12 | 2.0 | 2.1 | 2.8 |
| 20 | 6 | 3.9 | 4.4 | 4.7 | 5.8 |
| 9 | 4 | 2.9 | 2.20 | 4.8 | 12.1 |
| 4 | 1.7 | 1.0 | 3.7 | 7.7 | 12.4 |

Thus, the novel shape of the sensor of the present invention may be adjusted to obtain a desired signal depending upon the respective indices of refraction of the normal environment (when the sensor is not exposed to the analyte) and the analyte. Although FIG. 4 illustrates the preferred shape, it will be appreciated that other loop shapes are possible in accordance with the teachings of the present invention. In particular, other loop shapes wherein the loop is substantially closed may provide acceptable results.

Figure 11A:
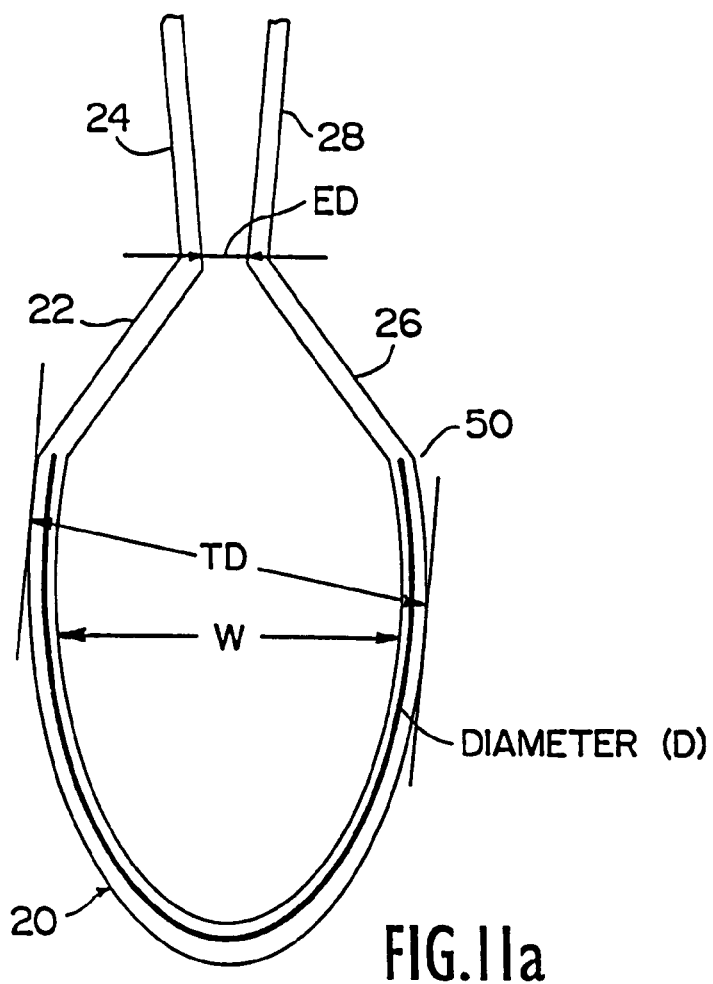
FIGS. 11a and 11b each illustrate a possible definition of a substantially closed loop that defines the sensor shape of the preferred embodiment of the present invention.
Figure 11B:
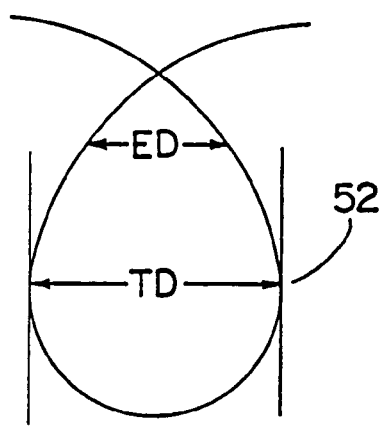

More formally, any loop allowing a signal to pass through it will have an input portion and an output portion which will in turn have a shortest distance (ED) therebetween measured in a plane. As used herein, a loop is any shape that curves back, in any plane, on itself. The loop is substantially closed if it has at least two tangent lines along the loop such that a distance (TD), measured by a line perpendicular to each of the tangent lines, exceeds ED, TD being measured in the same plane as ED. See FIGS. 11a and 11b, which illustrate, respectively, two possible substantially closed loop geometries 50 and 52. If a loop is not planar, as with the loop 52 in FIG. 11b, ED and TD must be projected onto an appropriate plane.

It should also be noted that the degree of curvature of the sensing segment 20 is an important parameter and may be derived from Table 1. Since in the preferred embodiment the sensing segment 20 comprises approximately a partial ellipse, the radius of curvature is not constant throughout the sensing segment 20. However, the minimum radius of curvature of an ellipse occurs at its apex points and is given for a particular apex by the formula $b^2/a$, where a is the length of the semi-major axis at the end of which the apex occurs and b is the length of the perpendicular semi-minor axis. Thus, $W^2/2C$ approximates the minimum radius of curvature at the apex of the sensor illustrated in FIG. 4.

Shapes other than the preferred partial ellipse of the present invention may be employed provided that any such shape has a segment with a sufficiently small minimum or average radius of curvature, as indicated by Table 1. For example, and in no way limiting the foregoing, a general U bend shape with a sufficiently small radius of curvature may be used in accordance with the teachings of the present invention.

The presently preferred method for fabricating the sensor is as follows. The ends of approximately 10 inches of unjacketed MORITEX fiber are inserted into a tie which is a short tube having an inside diameter of 5 mm and a length of 6 mm. By pulling the two ends with one hand and holding the tie with the other, the loop assumes a unique reproducible shape which can be characterized by W and L. For lengths which are less than 1" (L<1") it is necessary to use a smaller tie, 2.2 mm inside diameter and 3 mm long.

To shape fibers other than MORITEX into the configuration that results from the above process, a mold constructed from a thin sheet metal may be used. The outer surface of the mold is contoured to fit the inside of any one of the MORITEX sensors and the new sensor is formed by wrapping the optical fiber around the mold. If the desired material is glass, the fiber must be heated while it is wrapped around the mold.

To extrapolate the data of Table 1 to optical fibers having a diameter which is different than 1 mm, it is necessary to take into consideration that the light loss through the loop is inversely proportional the width W and directly proportional to the diameter of the fiber. (A decrease in W increases the bend curvature and therefore increases light loss. Increases in fiber diameter increases the circumferential area and thus increase light loss to the environment. ) As a first approximation, the scaling factor W/D=constant allows one to apply Table 1 to different fiber diameters. A sensor formed from a 2 mm fiber with W=4 mm will have the same loss as a sensor formed from a 1 mm fiber with W=2 mm. Obviously, since this scaling law is an approximation, adjustments may be required. Table 1 can be used as a guide for the relation between the length L and the width W to attain a desired sensitivity.

2. Interface Between the Sensor and its Environment

As previously mentioned, the strength of a signal (i.e. amount of loss or gain) when the analyte is present depends in part on the optical properties of the substances comprising the interface between the sensor 10 and the environment 11. According to the present invention and as illustrated in FIGS. 6a and 6b, the core or cladding of the fiber optic guide in the sensing segment 20 is coated with a coating that is selected to decompose in the presence of the analyte, as shown in FIGS. 6a and 6b. FIG. 6c shows a possible emobidment of the coating shown in FIG. 6a. The present invention provides for the dissolution of the coating when it comes into contact with a solute, a capability which is believed not to be found in prior art sensors. Further unlike prior art sensors, according to one embodiment of the present invention, the coating is selected to have an index of refraction just above or greater than the core (or cladding). Thus, in the presence of the analyte, less light escapes through the sensing portion 20, providing a signal that indicates the presence of the analyte.

In an alternate embodiment, the coating has an index of refraction lower than the fiber optic guide and particular coatings have been found to produce strong losses in the presence of the analyte. In yet another alternate embodiment, the coating swells, rather than dissolves, in the presence of the analyte, resulting in a change in the light reflection pattern at the fiber/coating interface. The increase in coating thickness due to swelling reduces back reflection from the coating/fluid interface and also changes the index of refraction of the coating and its absorption properties.

Table 2 shows how different coatings which separate the core (or cladding) from the environment 11 control light loss. For example, 30 dB leakage results from using GE Transparent RTV 108 as the coating. Removal of the coating in water results in a 15 dB change. As previously described, according to one embodiment, the coating may facilitate the transfer of light in the reverse direction, from the water to the fiber.

From the table, it should be noted that cladding removal is very effective in increasing loss. In general, cladding removal will reduce the monitoring distance but increase the sensitivity to changes in the index of refraction. By comparing cases A and D, the table indicates that cladding removal increases the loss to air by 3.7 dB and the loss to oil by 7.6 dB. If the sensors described by A and D were to be used to monitor the presence of oil in air, then sensor D will operate more reliably than sensor A because of its larger signal intensity, 9.7 dB vs 5.8 for sensor A.

On the other hand, the removal of the cladding reduces the available excess gain by 3.7 dB. To compensate for this loss, the monitoring distance may be reduced by about 10 meters, (corresponding to tube attenuation of 160 dB/km). The data of Table 1 allow the designer to make trade-off studies in selecting the optimum sensor for his or her specific application.

Table 2, referring to sensors E and F, shows that small sensors (Eg. w/d=2, L=4 mm, A=40 deg.) are capable of generating large signals. The 15 dB loss which was obtained when the coating was removed corresponds to a 97% increase in signal strength. This data illustrates how selective destruction of a coating in the sensing zone can provide strong recognition signals. Having this capability, the designer can use inexpensive light sources and detectors to distinguish recognition signals in environments with large background noise.

| Layer | Air | Water (dB) | 50% NaOH (dB) | Oil (dB) |
| --- | --- | --- | --- | --- |
| A | 5.6 | 10.1 | 10.6 | 11.4 |
| B | 5.8 | 9.0 | 10.6 | 10.8 |
| C | 7.0 | 10.1 | 13.3 | 14.4 |
| D | 9.3 | 16.9 | 19 | 19 |
| E |  | 30 |  |  |
| F |  | 15 |  |  |
| G | 22.2 |  |  |  |
| H | 33.1 |  |  |  |

Table 2—Effect of Control Layer on Leakage to various fluids (w/d=2.5 L=4 mm, A=40 deg)
All figures are referenced to a straight cladded plastic fiber with diameter D=1 mm A—5 micron cladding B—Cladding overlaid with saran wrap. C—1 mm of clad removed. D—4 mm of clad removed by slight scraping in the sensing zone. E—smear over sensing zone with GE RTV 108. F—RTV removed G—Smear over sensing zone with 3M-46, Industrial Adhesive. H—3M coat removed.

In the preferred embodiment, the coating comprises a polymer that dissolves or swells when the local pH changes (i.e. when the detectable substance is present) and further comprises enzymes that cause these changes in a selective manner. Reports on the use of polymer coated surfaces for sensing chemicals indicate that highly stable polymers are available. For example, the paper Calum McNeil et.al., "Electrochemical Sensor Based on Impedance Measurements of Enzyme Catalyzed Polymer Dissolution Theory and Application," Analytical Chem., vol 67, Nov. 21, 1995, demonstrates that the enzyme urease can catalyze urea to form products which de grade the polymer Eudragit S 100. Layers of 35 microns were destroyed in two minutes by a small concentration of urea.

In the preferred embodiment, a thin coating, approximately 5 microns, is used to facilitate the rapid degradation of the coating.

FIGS. 7a and 7b illustrate an alternate sensor/environment interface that is useful for "one shot" as opposed to continuous detection schemes. As shown in FIG. 7a, a selective polymer/enzyme mixture 40 is over coated with a water permeable membrane 42. As shown, exposure of the sensor to water causes the enzymes to degrade the molecular weight of the polymer, allowing water to come in contact with the fiber. When the water is contaminated with the analyte, however, as illustrated in FIG. 7b, enzyme activity is inhibited and the large polymer molecules are trapped by the membrane. Thus, the presence of the metal causes the sensor to come in contact with a highly concentrated polymer solution. When the analyte is absent, only water is in contact with the sensor. The different indices of refraction between water and the polymer solution result in different signals, depending upon the presence or absence of the analyte.

3. Alternate Sensor Geometry

In the above preferred embodiments, the physical shape of the sensor, i.e the loop of FIG. 2, was preset prior to exposure to the environment. Such designs are well suited for large core fibers, for example fibers with diameters that exceed 500 microns. (At present, smaller diameter fibers are easily breakable and therefore are not generally practical for harsh environments.) According to an alternate embodiment of the present invention, it is not necessary to expose the core and the cladding directly to the environment.

In this alternate embodiment, a short section of a commercial optical fiber is automatically bent in response to a contact with a specific substance such as a fluid. The bending of the fiber causes light loss to the environment and thereby reduces the amount of light which strikes a photodetector. This reduction in light intensity is used as the recognition signal. In the absence of the analyte, this sensor has no insertion loss.

Figure 12C:
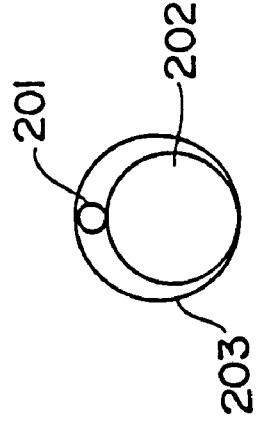
FIGS. 12a, 12b and 12c demonstrate an alternate sensor which automatically bends a fiber in response to the presence of a specific substance.
Figure 12B:
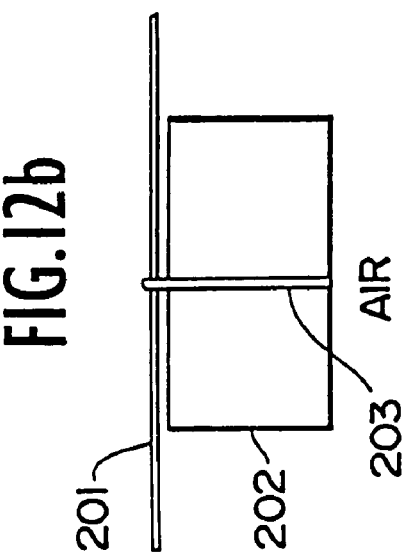
Figure 12A:
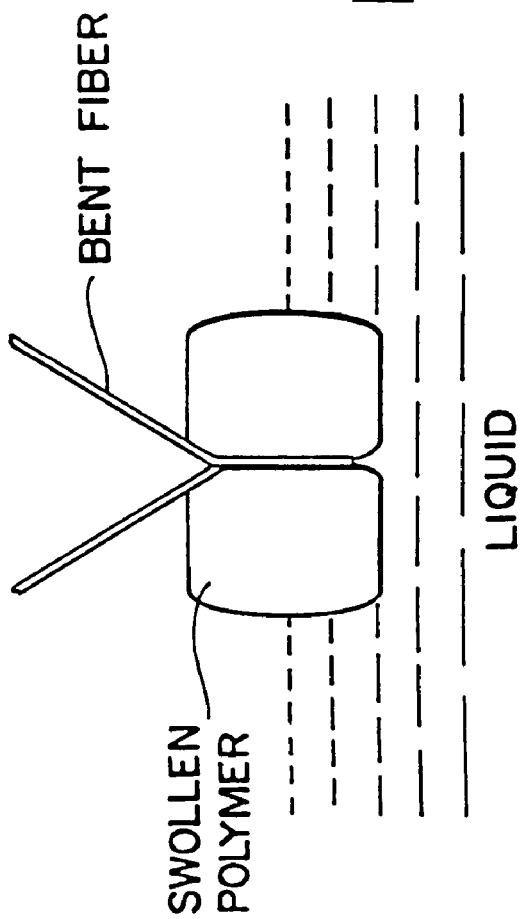

FIGS. 12a, 12b and 12c illustrate this alternate embodiment, which comprises a fiber optic guide 201 such as for example Corning 9/125 Singlemode 900 $\mu$m buffered, a cylindrically shaped short (½") polymer 202 such as natural rubber, and a standard wire 203 which is wrapped around the fiber 201 and the polymer 202. When the polymer 202 comes in contact with a specific substance such as a liquid, it swells and forces its body against the wire 203 gradually bending the fiber 201, eventually cutting it. The rate of bending can be controlled by the initial tightness of the wire 203 around the fiber 201 and the polymer 202. Use of the sensor illustrated in FIGS. 12a, 12b and 12c with glass fibers allows for sensing over very large distances (50 miles).

II. Applications

As previously described, the present invention comprises a sensor with a novel shape and novel interfaces between the sensor and its environment. The combination of these two mechanisms provides a simple, inexpensive, miniature size sensor which can produce strong signals.

The present invention is useful for detecting an almost unlimited number of substances. The following subsections describe preferred types of coatings and/or shapes for particular applications but it will be readily appreciated that the present invention has many other uses than those specifically described herein.

1. Detection of liquid interfaces

The sensor may be used to detect the presence of a particular liquid within another liquid. When one of the liquids has an index of refraction larger than 1.48, the optimum sensor width W is between 10 and 20 fiber diameters. When the index of refraction of the sensor's core is larger than the index of refraction of either fluid, the loop width W should be less than 5 fiber diameters. The length L of the loop is adjusted until the losses in the two fluids are different. Preferably, the clad from the apex region is removed for improved sensitivity.

2. Measurements of pH

The sensor may be used to measure pH levels. To sense pH levels, a suitable coating is chosen that dissolves at a desired pH level. For example, the solubility of many polymers, such as NIPAAm, depends on the pH of the solution. About five microns of polymer coating is recommended.

3. Measurements of Urea

The sensor may be used to detect urea. When the fluid pH is acidic the core of the sensor is coated with at least 5 microns of enteric polymer/urease complex. Preferably, the loop length L does not exceed 5 fiber diameters and the coating comprises the materials specified in the aforementioned paper by Calum McNeil.

For the detection of urea in blood at a patient's bedside, the sensor of the present invention is used in conjunction with the procedure described in the McNeil paper. Commercially available Eudragit S 100 polymer is dissolved in 13.7 g acetone containing 0.25 g of dibutyl phtalate. This mixture is sprayed over the polymer at several intervals to allow each layer to solidify before the next is applied. The enzyme Urase is then immobilized in a thin cellulose membrane which is attached to the polymer. In the presence of urea, the polymer will dissolve, allowing blood to contact the core. The resulting signal can be sent directly to a doctor's office.

4. Detection of Trace Heavy Metals in Water

To detect trace heavy metals in water, the embodiment illustrated in FIGS. 7a and 7b may be used. F or the detection of heavy metals, the most suitable enzymes are those which contain a bound metal ion. For example, the enzyme mannanase is strongly inhibited by silver and mercury ions. A mixture of mannan with mannanase and salt additives for the desired index of refraction, provides the proper coating for the detection of the above chemicals. Cellulose can be used to construct a simple sensor. The literature provides a large list of polymers and the corresponding enzymes which will reduce their molecular weight: mannan/mananas, starch/amylase, protein/protease, DNA/DNAse, RNA/RNAse, xylan/xylanase, glucan/endoglucanase, CMS/endocellulase, pectin/pectinase, pullulan/pullulanase. Microfilters are available from Gelman Sciences, Sartorius AG, Millipore, Inc. These filters are stable and are made of materials such as nylon 66, 0.2 $\mu$m (Rainin) and cellulose acetate 0.22 $\mu$m (Millipore, type GS). These filters will allow water to pass through but prevent molecules of certain size from passing through.

5. Detection of Antigens in Drinking Water.

As described in Schultz, "Biosensors," Scientific American (August 1991), specific antibodies may be immobilized on the surface of a fiber optic core. When the sensor is exposed to drinking water, antigens will bind to the antibodies on the surface and the thickening of the antibody/antigen layer changes the effective index of refraction of the water at the core surface. The sensor of the present invention enhances the effectiveness of the technique described in the Schultz article by combining that technique with a sensor with a preferred W/D ratio of less than 2 and A=45 degrees.

III. Large Scale System Configuration

This section of the application will describe configurations of the sensor within different systems designed to detect various substances.

1. In-Situ Continuous Pollution Monitoring

One application of the present invention is to perform continuous in situ remote monitoring of various environmental sites. By inserting several sensors in and near a bore hole as shown in FIGS. 8a and 8b, the ground water and the soil can be continuously monitored for the presence of contaminants. Each sensor is connected to an electronic unit which incorporates a light source a photodetector and an amplifier. Such electronic packages are available commercially from Cutler Hammer, Comet 100, for example, and are specifically designed for plastic fibers. The output from the Comet 100 can be connected to a telephone line through a transmitter. The appearance of a contaminant will activate the transmitter and convey the information to the owner in his office. In this example, we use three different sensors, one to detect the appearance of thin oil layers above water, the second to monitor pH changes in the water and the third to detect chemicals such as heavy metals and cyanide in the soil. For the detection of oil, the sensor of FIG. 4 (w/d=11) is mounted on a float as shown in FIG. 8. For the detection of pH changes, the sensor of FIG. 4 is mounted on the same float. The core of this sensor is coated with a pH sensitive polymer.

For the detection of heavy metals, two sensors of the type shown in FIGS. 7a and 7b, with L<5 and W/D<5, are inserted into soil. The sensors are attached to each other with their tips spaced within 1 mm. The core of one sensor is left uncoated while the core of the other is coated with a biopolymer. Both sensors will provide the same signal when the metal is absent. The signal intensities will be different when the metal is present.

2. Remote Detection of Leaks From Petroleum Tanks.

Figure 10:
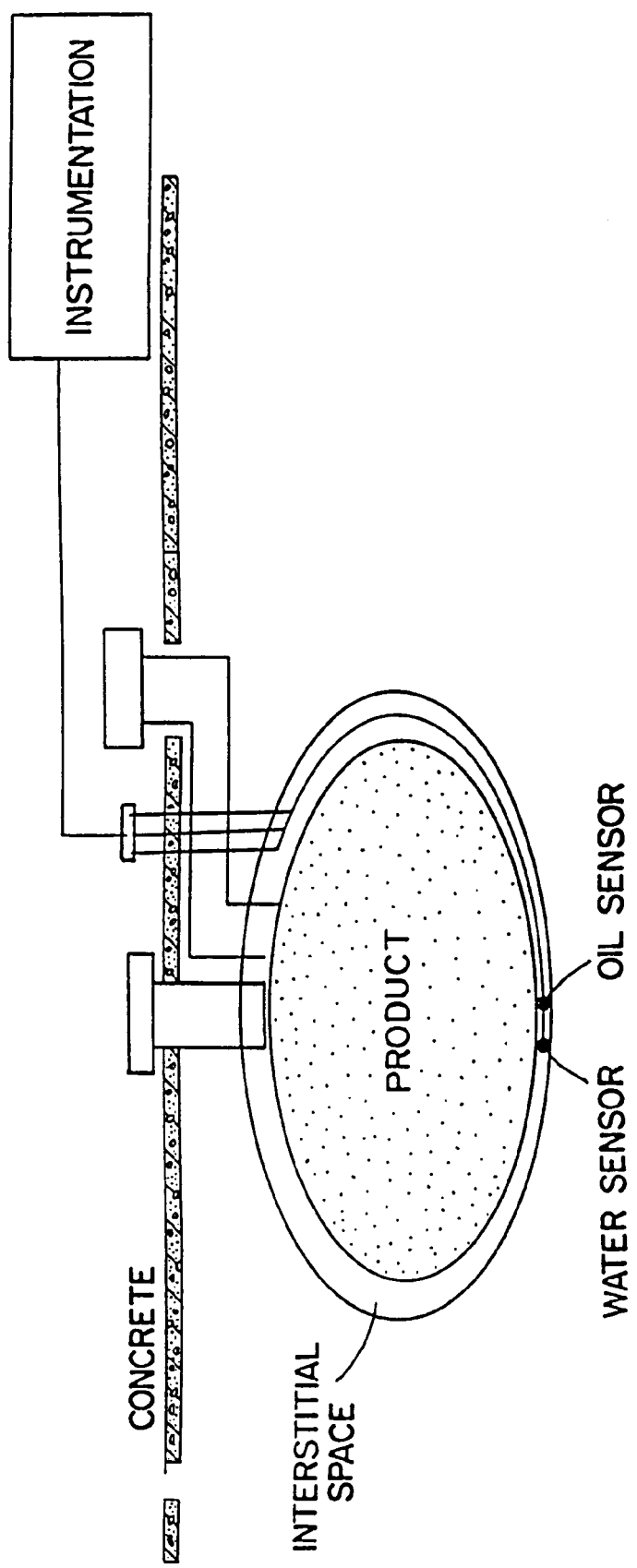
FIG. 10 illustrates a system to use sensors for detecting oil and water in tanks.

To detect the presence of leaks, two uncoated sensors are placed in the interstitial space of the storage tank, as illustrated in FIG. 10. The sensor for the detection of product only has a w/d ratio of 10 while the sensor for the detection of water or product has a w/d ratio of about 2.5. If water enters the interstitial space from condensation or from a failure of the outer surface of the tank only the small sensor will be activated. When a leak is developed on the product side both sensors will generate signals.

3. Remote Detection of Oil Spills in Sumps.

Sumps in powerplants can be subjected to oil spills from failed electrical transformers. This potential source of pollution can be minimized if the pumps are turned off as soon as the spill occurs. FIGS. 9a, 9b, 9c and 9d show a system which warns operators of an oil spill. A sensor (W/D=10) is mounted on a floating platform. One of the floats anchors the platform to a PVC pipe and the other two floats assure that the sensor is positioned at the water surface. The sensor position can vary within 0.22" of the water surface and still accurately detect the presence of oil within this distance. A sensor 118 is connected through an optical fiber 114 to an instrumentation box 111 which contains the controller and the pump relay. The fiber 114 is protected by pvc tubing 112 and 114. A PVC pipe 115 acts as a guide and an anchor for the platform.

Conclusion

While the invention has been described in conjunction with the preferred embodiment, it is evident that numerous alternatives, modifications, variations and uses will be apparent to those skilled in the art in light of the foregoing description. The scope of the invention should thus be measured by the following claims.

I claim:

1. A method for detecting the presence or absence of a particular substance in an environment, the method comprising the steps of:

providing a fiber optic guide having at least at some point along its length between a first end and a second end a coating that has an index of refraction greater than the index of refraction of the fiber optic guide, the coating having a composition such that it at least partially degrades in the presence of a substance to be detected such that the amount of coating on the fiber optic guide decreases;

transmitting light through the first end of the fiber optic guide;

detecting light from the second end of the fiber optic guide, the step of detecting light including the step of detecting an increase in the intensity of light at the second end when the presence of the substance to be detected is brought into contact with the fiber optic guide.

2. The method of claim 1 wherein the coating comprises GE RTV 108.

3. The method of claim 1 wherein:

the fiber optic guide comprises a core and a cladding;

the fiber optic guide comprises a sensing portion and the cladding is absent from the sensing portion; and the coating covers the core in the sensing portion.

4. The method of claim 1 wherein the fiber optic guide comprises a core and a cladding and the coating covers the cladding.

5. The method of claim 1 wherein the intensity of light at the second end is greater when the substance to be detected is introducted into the environment.

6. A method for detecting the presence or absence of a particular substance in an environment, the method comprising the steps of:

providing a fiber optic guide having at least at some point along its length between a first end and a second end a coating that has an index of refraction different than the index of refraction of a portion of the environment, the coating having a composition such that it degrades more in the absence of a substance to be detected than in the presence of the substance to be detected;

transmitting light through the first end of the fiber optic guide;

detecting light from the second end of the fiber optic guide, the step of detecting light including the step of detecting an intensity of light at the second end, the intensity detected being different if the substance to be detected is not brought into contact with the coating compared to the intensity detected if the substance to be detected is brought into contact with the coating.

7. The method of claim 6 wherein the coating is covered with a selectively permeable membrane.

8. The method of claim 7 wherein the membrane is permeable to water.

9. The method of claim 6 wherein the coating comprises polymers.

10. The method of claim 9 wherein the coating further comprises enzymes such that the coating comprises a polymer enzyme pair, the enzymes having a composition such that they degrade the polymers in the absence of the substance to be detected and do not degrade the polymers in the presence of the substance to be detected, whereby the polymers pass through the membrane in the absence of the substance to be detected.

11. The method of claim 10 wherein the polymer/enzyme pair is selected from the group consisting of: mannan/mananas, starch/amylase, protein/protease, DNA/DNAse, RNA/RNAse, xylan/xylanase, glucan/endoglucanase, CMS/endocellulase, pectin/pectinase, or pullulan/pullulanase.

12. The method of claim 6 wherein the portion of the environment is water.

13. A method for detecting the presence or absence of a particular substance in an environment, the method comprising the steps of:
    providing a fiber optic guide having at least at some point along its length between a first end and a second end a coating that has an index of refraction less than the fiber optic guide, the coating having a composition such that it at least partially degrades in the presence of a substance to be detected such that the amount of coating on the fiber optic guide decreases;
    transmitting light through the first end of the fiber optic guide, at least some of the light passing through the coating and into the environment when the substance to be detected is not present in the environment;
    detecting light from a second end of the fiber optic guide, the step of detecting light including the step of detecting a decrease in the intensity of light at the second end when the substance to be detected is introduced into the environment.

14. The method of claim 13 wherein the coating has an index of refraction of at least 1.4 but not in excess of 1.6.

15. A method for detecting the presence or absence of a particular substance in an environment, the method comprising the steps of:
    providing a fiber optic guide having at least at some point along its length between a first end and a second end a coating comprising a first material, the coating being covered with a selectively permeable material such that the flux of the first material through the covering depends on whether a substance to be detected is brought into contact with the coating;
    transmitting light through the first end of the fiber optic guide;
    detecting light from the second end of the fiber optic guide, the step of detecting light including the step of detecting an intensity of light at the second end, the intensity detected being different if the substance to be detected is not brought into contact with the coating compared to the intensity detected if the substance to be detected is brought into contact with the coating.

16. The method of claim 15 wherein the covering comprises a membrane.

17. The method of claim 15 wherein the first material comprises polymers and enzymes and wherein the enzymes tend to inhibit degradation of the polymers in the presence of the substance to be detected.

18. The method of claim 15 wherein the flux of the first material through the covering is greater when the substance to be detected is not brought into contact with the coating compared to the intensity detected if the substance to be detected is brought into contact with the coating.

19. The method of claim 15 wherein the covering is in contact with the coating before the fiber optic sensor is provided in the environment.

* * * * *